US009586205B2

(12) United States Patent
Asogawa et al.

(10) Patent No.: US 9,586,205 B2
(45) Date of Patent: Mar. 7, 2017

(54) ANALYSIS DEVICE

(71) Applicant: NEC Corporation, Minato-ku, Tokyo (JP)

(72) Inventors: Minoru Asogawa, Tokyo (JP); Yoshinori Mishina, Tokyo (JP); Yasuo Iimura, Tokyo (JP); Hisashi Hagiwara, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 14/432,812

(22) PCT Filed: Jul. 8, 2013

(86) PCT No.: PCT/JP2013/004213
§ 371 (c)(1),
(2) Date: Apr. 1, 2015

(87) PCT Pub. No.: WO2014/054207
PCT Pub. Date: Apr. 10, 2014

(65) Prior Publication Data
US 2015/0251180 A1    Sep. 10, 2015

(30) Foreign Application Priority Data

Oct. 1, 2012  (JP) .................................. 2012-219262

(51) Int. Cl.
*G01N 27/00* (2006.01)
*B01L 3/00* (2006.01)
(Continued)

(52) U.S. Cl.
CPC .. *B01L 3/502715* (2013.01); *G01N 27/44704* (2013.01); *G01N 27/44713* (2013.01);
(Continued)

(58) Field of Classification Search
CPC ........... B01L 3/502715; B01L 3/50273; G01N 27/44791; G01N 27/44704
(Continued)

(56) References Cited

U.S. PATENT DOCUMENTS 3,658,478 A * 4/1972 Spergel ................. G01N 35/00
204/402
3,818,678 A * 6/1974 Gothard ..................... B03C 3/04
95/75
2010/0200402 A1* 8/2010 Li ....................... G01N 35/1095
204/451

FOREIGN PATENT DOCUMENTS

JP          62-115167 U    7/1987
JP         2003-508043 A   3/2003
(Continued)

OTHER PUBLICATIONS

International Search Report for PCT Application No. PCT/JP2013/004213, mailed on Sep. 17, 2013.

*Primary Examiner* — Thanh-Truc Trinh

(57) ABSTRACT

An analysis chip device according to an exemplary embodiment of the present invention includes a placing board (17) on which a microchip (14) is placed, and a coupling (20) attached to a cover (11) of the microchip (14). The coupling (20) includes a linear electrode (25), a sleeve (22) including an attach part (28) that is attached to the cover (11) and an air core part (23) in which the electrode (25) is provided, the sleeve (22) having a side surface in which an inlet port (26) is provided, the inlet port (26) communicating with the air core part (23); and a holder (21) including a pipe connection part (27) to which a pipe (32) is connected, the pipe (32) supplying gas to the inlet port (26), the holder (21) holding the sleeve (22) so as to surround the inlet port (26).

5 Claims, 5 Drawing Sheets

(51) Int. Cl.
*G01N 27/447* (2006.01)
*G01N 35/00* (2006.01)
*B01L 7/00* (2006.01)

(52) U.S. Cl.
CPC .......... *G01N 27/44791* (2013.01); *B01L 7/52* (2013.01); *B01L 2200/027* (2013.01); *B01L 2200/10* (2013.01); *B01L 2300/0645* (2013.01); *B01L 2300/0816* (2013.01); *B01L 2300/0864* (2013.01); *B01L 2300/0867* (2013.01); *B01L 2300/1822* (2013.01); *B01L 2400/0421* (2013.01); *G01N 2035/00158* (2013.01)

(58) Field of Classification Search
USPC ........ 204/603, 604, 452, 453; 422/502, 503, 422/545, 564, 82.01
See application file for complete search history.

(56) References Cited

FOREIGN PATENT DOCUMENTS

| | | | | |
|---|---|---|---|---|
| JP | 2003524183 A | | 8/2003 | |
| JP | 2007-021366 | * | 2/2007 | .............. B01J 19/00 |
| JP | 2007-107916 A | | 4/2007 | |
| JP | 2010-528264 A | | 8/2010 | |

* cited by examiner

ANALYSIS DEVICE

This application is a National Stage Entry of PCT/JP2013/004213 filed on Jul. 8, 2013, which claims priority from Japanese Patent Application 2012-219262 filed on Oct. 1, 2012, the contents of all of which are incorporated herein by reference, in their entirety.

TECHNICAL FIELD

The present invention relates to an analysis device, and more particularly, to an analysis device that includes a coupling.

BACKGROUND ART

A device to specify a gene locus by electrophoresis is disclosed (Patent literature 1). The device disclosed in Patent literature 1 includes a microlocation substrate and a capillary tube. The capillary tube is made of platinum. Patent literature 1 further discloses that CO2 is supplied to a coaxial tube.

CITATION LIST

Patent Literature

Patent Literature 1: Published Japanese Translation of PCT International Publication for Patent Application, No. 2003-508043

SUMMARY OF INVENTION

Technical Problem

Patent literature 1 does not disclose, however, a specific configuration to supply gas and a voltage to a chip.

The present invention aims to provide an analysis device capable of supplying gas and a voltage at the same time.

Solution to Problem

An analysis chip device according to one exemplary aspect of the present invention includes: a placing board on which a chip is placed, the chip being supplied with a sample; and a coupling that is attached to a cover, the cover covering the chip, in which: the coupling includes: a linear electrode; a sleeve including an attach part that is attached to the cover and an air core part in which the electrode is provided, the sleeve having a side surface in which a gas inlet port is provided, the gas inlet port communicating with the air core part; and a holder including a pipe connection part to which a pipe is connected, the pipe supplying gas to the gas inlet port, the holder holding the sleeve so as to surround the gas inlet port.

Advantageous Effects of Invention

According to the present invention, it is possible to provide an analysis device capable of supplying gas and a voltage at the same time.

DESCRIPTION OF EMBODIMENTS

With reference to the accompanying drawings, exemplary embodiments of the present invention will be described. The exemplary embodiments described below are examples of the present invention, and the present invention is not limited to the following exemplary embodiments. In this specification and the drawings, the same elements are denoted by the same reference symbols.

Figure 1:
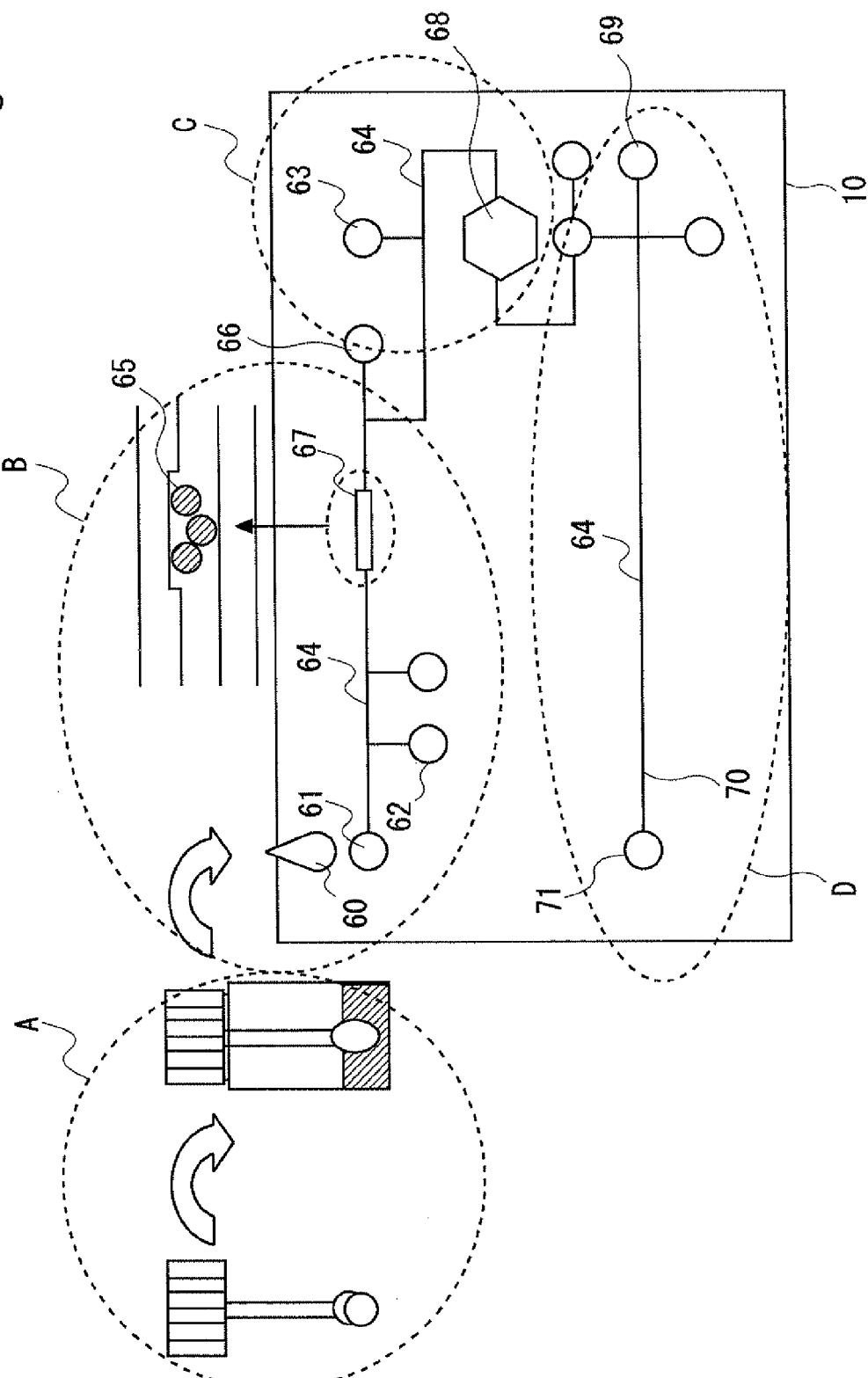
FIG. 1 is a view schematically showing each process of a DNA analysis according to an exemplary embodiment of the present invention.
Figure 2:
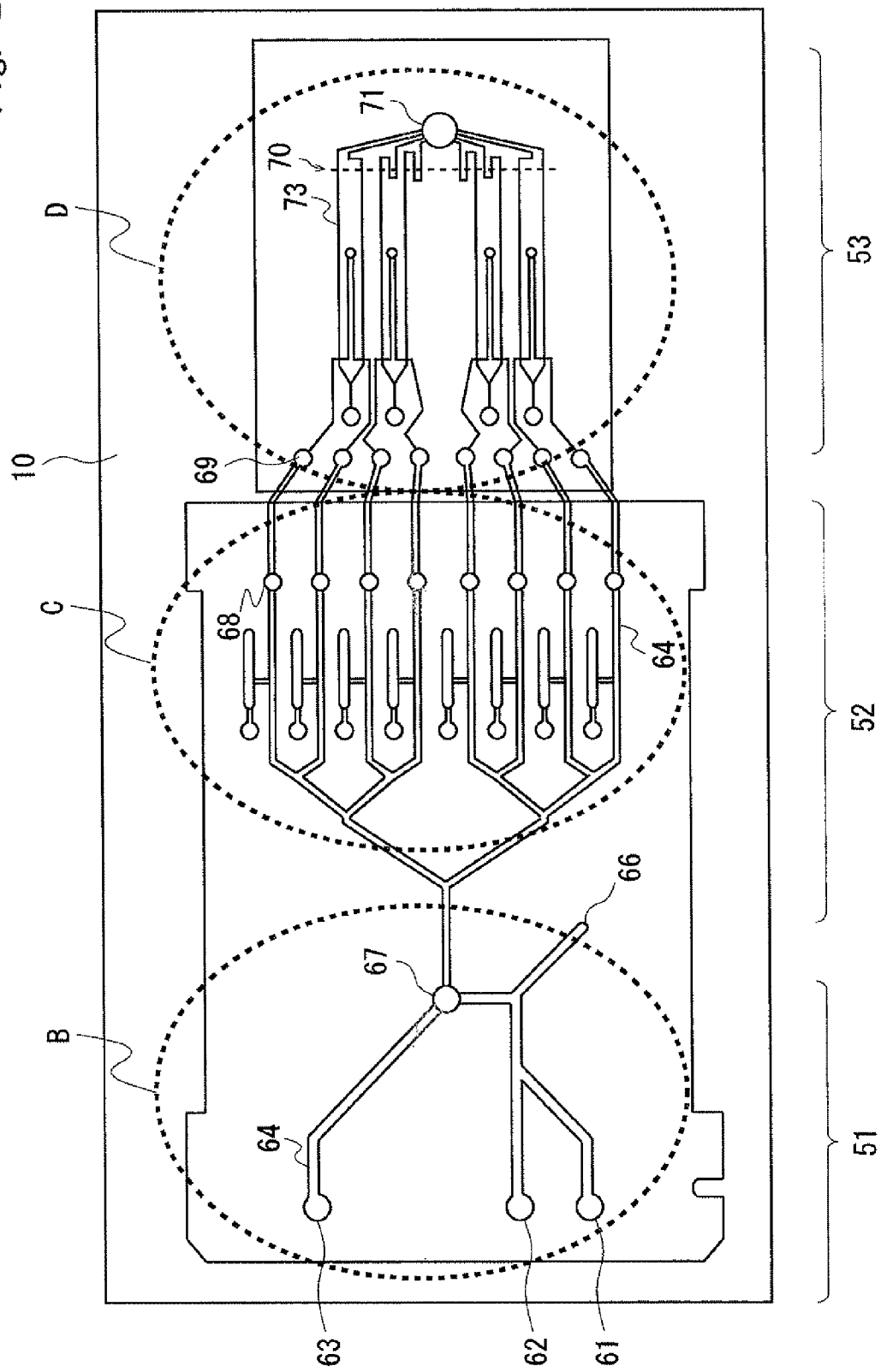
FIG. 2 is a plane view schematically showing a configuration of an analysis chip used for the DNA analysis.

An analysis device according to an exemplary embodiment is an analysis device that carries out an analysis using an analysis chip device for carrying out a DNA analysis by electrophoresis. With reference to FIGS. 1 and 2, a method for carrying out the DNA analysis using the analysis chip device will be described below. FIG. 1 is a view schematically showing processes of the DNA analysis using an analysis device according to the exemplary embodiment. FIG. 2 is a plane view schematically showing a configuration of the analysis chip.

As shown in FIG. 1, the DNA analysis method includes a specimen collection process A, a DNA extraction process B, a PCR amplification process C, and an electrophoretic process D. The specimen collection process A is executed in the outside of an analysis chip 10, and the DNA extraction process B, the PCR amplification process C, and the electrophoretic process D are executed in the analysis chip 10.

As shown in FIG. 2, a DNA extraction region 51 in which the DNA extraction process B is executed is provided on an upstream side (left side in FIG. 2) of the analysis chip 10. A PCR amplification region 52 in which the PCR amplification process C is executed is provided on a downstream side (right side in FIG. 2) of the DNA extraction region 51. An electrophoresis region 53 in which the electrophoretic process D is executed is provided on a downstream side of the PCR amplification region 52. DNA, which is a sample, is transferred through the DNA extraction region 51, the PCR amplification region 52, and the electrophoresis region 53 in this order.

In the specimen collection process A, first, a user collects a cell including DNA, which is a sample. The user collects, for example, oral mucosa, blood, or body fluid. Then the cell is disrupted using a reagent to prepare a solution in which DNA is eluted.

In the DNA extraction process B, a solution 60 in which DNA is eluted is injected into the analysis chip 10. The analysis chip 10 includes a sample injection tank 61, a wash solution injection tank 62, a PCR reagent injection tank 63, a channel 64, magnetic beads 65, an outlet 66, a reaction tank 68, a phoresis tank 69, and a phoresis tank 71. The sample injection tank 61, the wash solution injection tank 62, the PCR reagent injection tank 63, the magnetic beads 65, the outlet 66, the reaction tank 68, the phoresis tank 69, and the phoresis tank 71 communicate with one another via the channel 64. That is, the solution 60 is sequentially transferred through the tanks via the channel 64. The channel 64 is narrower than the tanks.

The solution 60 including DNA, which is the sample, is injected into the sample injection tank 61. A wash solution to clean the channel 64 and the like is injected into the wash solution injection tank 62. The solution 60 injected from the sample injection tank 61 is delivered to an extraction part 67 via the channel 64. The magnetic beads 65 to entangle DNA are provided in the extraction part 67. A surface of the magnetic beads 65 has a property of having good compatibility with DNA. Accordingly, by mixing the magnetic beads 65 with the solution 60 in which DNA is eluted, DNA is entangled in the magnetic beads 65. After that, the magnetic beads 65 are cleaned using the wash solution. By using magnets, the magnetic beads 65 can be easily immobilized. Then only DNA is transferred to the next PCR reaction tank 68. Residual wash solution and the like are discharged from the outlet 66.

A PCR reagent that amplifies a specific gene locus is injected into the PCR reagent injection tank 63. The PCR reagent injected into the PCR reagent injection tank 63 is delivered to the PCR reaction tank 68. In the PCR reaction tank 68, DNA is amplified by a polymerase chain reaction (PCR). In this example, as shown in FIG. 2, eight PCR reaction tanks 68 are provided. DNA is then dispensed into the eight PCR reaction tanks 68 together with the PCR reagent. By using two kinds of PCR reagents, 16 (2×8) gene loci can be analyzed at one time.

For example, a temperature control element (not shown) such as a Peltier element is provided immediately below the PCR reaction tank 68. By repeating a predetermined temperature cycle by the temperature control element, only repeated portions of the gene locus can be amplified. Specifically, DNA is PCR-amplified by the temperature control element repeating heating and cooling. Further, the PCR reagent contains fluorescent substances used for labeling. The fluorescent substance used to label DNA may be, for example, 5-FAM, JOE, NED, and ROX. It is thus possible to label a specific base.

The PCR products amplified in the PCR reaction tank 68 are delivered to the phoresis tank 69. The phoresis tank 69 is connected to the phoresis tank 71 via the channel 64. Specifically, the PCR products transferred to the phoresis tank 69 migrate to the phoresis tank 71 via the channel 64. A voltage is applied between the phoresis tank 69 and the phoresis tank 71. Since DNA is negatively charged, DNA migrates to the phoresis tank 71 on the cathode side. The channel 64 between the phoresis tank 69 and the phoresis tank 71 is an extremely thin capillary 73 having a thickness of about 100 μm.

As described above, a voltage is applied between the phoresis tank 69 and the phoresis tank 71. The PCR products labeled by fluorescence are supplied to the capillary and are electrophoresed in gel. In a state in which a voltage is applied by electrophoresis, the migration velocity varies depending on the size of the DNA fragments. The migration distance increases with a decreasing number of bases. It is therefore possible to separate the DNA fragments by size. When PCR products in the capillary are irradiated with excitation light emitted from a light source at a detection position 70 which is between the phoresis tank 69 and the phoresis tank 71, fluorescence is generated from fluorescent substances. The fluorescence generated from the fluorescent substances is spectroscopically measured to obtain observed spectral data. The observed spectral data is obtained for each size of the DNA fragments, or each migration velocity. By analyzing these observed spectral data, it is possible to quantify DNA of a particular sequence and to execute DNA testing.

Further, while the analysis chip is used for DNA testing according to this exemplary embodiment, the analysis chip according to this exemplary embodiment is not limited to being applied to the DNA testing. The analysis chip according to this exemplary embodiment can be applied to various analysis devices. It is possible, for example, to apply the analysis chip to analysis devices which analyze nucleic acid, proteins, compounds and the like. Further, it is possible to label the substances included in the sample by labeled substances other than the fluorescent substances. Further, the analysis may be performed using other methods than spectroscopy.

Figure 3:
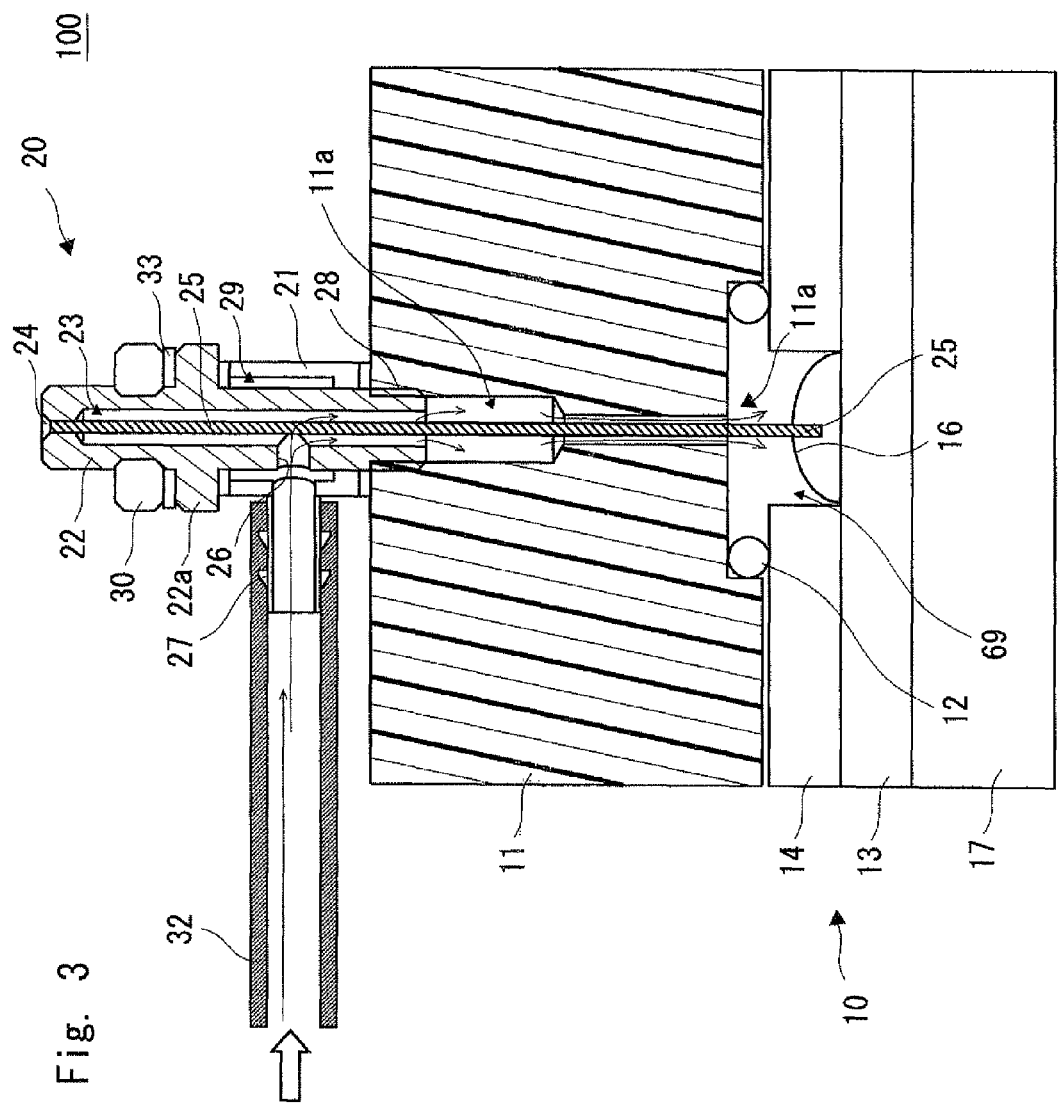
FIG. 3 is a side surface view showing a configuration of a coupling connected to the analysis chip.

In order to transfer gel or the sample which is in the phoresis tanks 69 and 71, pressurized gas needs to be supplied. Accordingly, a coupling to supply the gas is attached to each of the phoresis tanks 69 and 71. Further, an electrode to apply the voltage to the phoresis tanks 69 and 71 is needed. With reference to FIG. 3, a configuration of the coupling that includes the electrode to apply the voltage to the phoresis tanks 69 and 71 will be described. FIG. 3 is a side cross-sectional view showing a configuration of the analysis device in a state in which the analysis chip 10 is arranged. In FIG. 3, the vertical direction is a thickness direction of the analysis chip and the horizontal direction is a plane direction of the analysis chip.

An analysis chip device 100 includes the analysis chip 10, a cover 11, a seal 12, and a coupling 20. The analysis chip device 100 is placed on a placing board 17 of the analysis device. For example, the cover 11 is attached to the analysis chip 10 in a state in which the analysis chip 10 is placed on the placing board 17. The analysis chip 10 can be exchanged with another analysis chip as appropriate depending on the target to be analyzed or the analysis method.

The analysis chip 10 includes a base plate 13, a microchip 14, and a sheet 16. The microchip 14 is placed on the base plate 13 made of metal or the like. Further, the sheet 16 is interposed between the base plate 13 and the microchip 14. The microchip 14 is made of resin or the like and includes the phoresis tank 69. Further, the channel 64, the sample injection tank 61, the wash solution injection tank 62, the PCR reagent injection tank 63, the outlet 66, the extraction part 67, the PCR reaction tank 68, the phoresis tank 71 and the like described above are formed in the microchip 14. That is, a groove which is the channel 64 or storage tanks that store the sample are formed in the microchip 14. The sample flows through a space between the base plate 13 and the sheet 16. When the sample is stored in the sample tank 69, for example, the sheet 16 swells upward. That is, in the sample tank 69, a space to store the sample is formed between the sheet 16 and the base plate 13.

The cover 11 that covers the microchip 14 is provided on the microchip 14. The cover 11 can be formed, for example, of an insulator such as an acrylic board. A through hole 11a is provided in the cover 11. The through hole 11a is arranged immediately above the phoresis tank 69. Accordingly, the phoresis tank 69 communicates with the external space through the through hole 11a. Therefore, the phoresis tank 69 is supplied with gas such as nitrogen gas or air from a pipe 32 via the through hole 11a. Further, the seal 12 is provided on the microchip 14. The seal 12 is provided around the phoresis tank 69.

The seal 12 is interposed between the cover 11 and the microchip 14, so that the gap between the cover 11 and the microchip 14 is sealed around the phoresis tank 69. The seal 12 is provided in a depression formed in the cover 11.

The coupling 20 includes a holder 21, a sleeve 22, and an electrode 25. The coupling 20 is connected to the analysis chip 10. The holder 21 is a metal member that includes a hollow part 29. The sleeve 22 is provided in the hollow part 29 of the holder 21. That is, the sleeve 22 is inserted in the holder 21. A pipe connection part 27 is provided on a side surface of the holder 21. The pipe connection part 27 extends laterally from the side surface of the holder 21. As stated above, the pipe connection part 27 is provided in one end of the holder 21.

The pipe connection part 27 is connected to the pipe 32. For example, the pipe connection part 27 is inserted into the pipe 32, whereby the pipe 32 is fixed to the pipe connection part 27. Gas to transfer the sample which is in the phoresis tank 69 is supplied from the pipe 32 (arrow in FIG. 3). The gas from the pipe 32 is sent to the holder 21 through the hollow part of the pipe connection part 27. The upstream side of the pipe 32 is connected to a gas supply source via a control valve or the like. The supplying or the stopping of the gas can be controlled by controlling the control valve. It is therefore possible to control the transfer of the sample.

The sleeve 22 penetrates through the holder 21 in the vertical direction. The sleeve 22 can be formed of, for example, gold plated brass. The sleeve 22 is a substantially cylindrical member having an air core part 23. Further, the sleeve 22 has a wide part 22a so that a part of the sleeve 22 has a wide width. The air core part 23 is provided along the vertical direction. A linear electrode 25 is arranged in the air core part 23. The electrode 25 can be formed of a platinum wire having a diameter of about 0.5 mm. The electrode 25 has a straight shape so as to extend in the vertical direction through the air core part 23. That is, the electrode 25 is arranged along the air core part 23.

The electrode 25 extends below the lower end of the sleeve 22. That is, the electrode 25 has a length different from that of the sleeve 22 and projects to the bottom surface side of the analysis chip 10 further than the sleeve 22. The electrode 25 passes through the air core part 23 and reaches the through hole 11a. Further, the electrode 25 passes through the through hole 11a and reaches the phoresis tank 69. That is, the electrode 25 has such a length that the lower end of the electrode 25 is lower than the upper surface of the microchip 14. The electrode 25 penetrates through the sheet 16 which swells upward. Therefore, the lower end of the electrode 25 contacts the gel in the phoresis tank 69. Accordingly, the voltage for electrophoresis can be applied to the gel including DNA. The voltage can also be applied to the liquid sample that flows between the sheet 16 and the base plate 13.

A fixing part 24 to fix the electrode 25 is provided in the upper end of the sleeve 22. In the fixing part 24, the sleeve 22 and the electrode 25 are fixed to each other by welding or soldering. It is therefore possible to fix the sleeve 22 and the electrode 25 and to seal the upper end of the air core part 23. Further, since the fixing part 24 is welded or soldered, the sleeve 22 can be electrically connected with the electrode 25.

An attach part 28 to attach the sleeve 22 to the cover 11 is provided in the lower end of the sleeve 22. A screw groove, for example, is provided in the attach part 28. Further, the upper part of the through hole of the cover 11 is a screw hole. By screwing the sleeve 22 into the through hole 11a, the sleeve 22 can be fixed to the cover 11. As described above, by providing the screw groove in the attach part 28, the coupling 20 can be easily attached to the cover 11. As a matter of course, the coupling 20 can be attached to the analysis chip 10 by a mechanism other than the screw structure.

An inlet port 26 to introduce gas is provided on the side surface of the sleeve 22. The space outside of the sleeve 22 and the air core part 23, which is the space inside the sleeve 22, communicate with each other through the inlet port 26. The inlet port 26 is formed so as to have a height such that the inlet port 26 is disposed in the holder 21. Accordingly, the gas supplied to the hollow part 29 of the holder 21 from the pipe connection part 27 passes through the inlet port 26 to reach inside the air core part 23. Further, the gas passes through the through hole 11a from the air core part 23 to be supplied to the phoresis tank 69. When the gas is supplied to the phoresis tank 69, fluid such as gel which is inside the phoresis tank 69 is sent to the channel. In this example, the pipe connection part 27 and the inlet port 26 face each other. The holder 21 holds the sleeve 22 to surround the inlet port 26.

The lower end of the coupling 20 is in the middle of the through hole 11a. Accordingly, the gas supplied from the pipe 32 applies a stress to the sample through the sheet 16. Therefore, the gas from the coupling 20 is supplied to the space above the sheet 16. The sample between the sheet 16 and the microchip 14 receives the stress through the sheet 16. Therefore, the sample stored in the phoresis tank 69 flows through the channel.

Further, the sleeve 22 has the wide part 22a in the middle thereof. That is, the middle part of the sleeve 22 in the vertical direction is wide. In the wide part 22a, the sleeve 22 is extended outwardly and the width of the sleeve 22 is large. The wide part 22a is larger than the outer diameter of the holder 21. Therefore, the holder 21 is arranged in the lower side of the wide part 22a. In other words, the holder 21 is held between the wide part 22a and the cover 11. The wide part 22a has a shape of a hexagon nut so that the sleeve 22 can be fastened to the cover 11 using the attach part 28.

A bus plate 33 is arranged on the wide part 22a. The bus plate 33 is a bus electrode to electrically connect the electrodes 25 of the plurality of couplings 20, and is formed of, for example, a metal plate. The bus plate 33 has a hole having a diameter smaller than that of the wide part 22a of the sleeve 22. The upper part of the sleeve 22 is inserted into the hole in the bus plate 33. The bus plate 33 is held on the wide part 22a. The bus plate 33 is a metal plate to apply a voltage from the outside. A nut 30 is arranged on the bus plate 33. The nut 30 is screwed into a screw groove arranged on the upper side of the sleeve 22. Accordingly, the bus plate 33 is fixed between the wide part 22a and the nut 30 by the nut 30. Since the bus plate 33, the sleeve 22, and the electrode 25 are made of metal, they are electrically connected one another. The voltage applied to the bus plate 33 is applied to the electrode 25 via the sleeve 22. It is therefore possible to supply a predetermined voltage to the sample.

Figure 4:
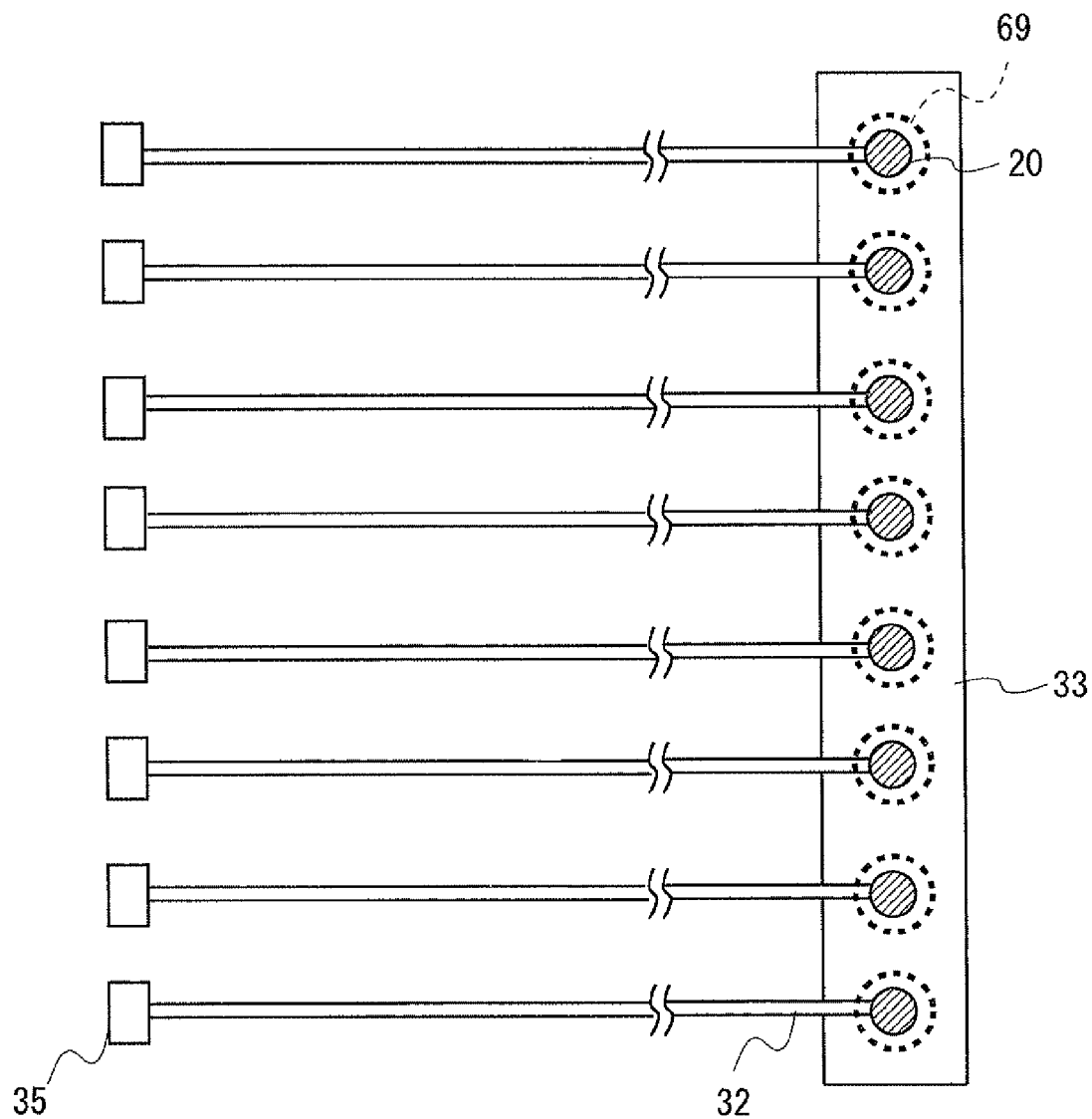
FIG. 4 is a plane view schematically showing a configuration to electrically connect electrodes by couplings.

Further, a plurality of couplings 20 may be connected by the bus plate 33. This configuration will be described with reference to FIG. 4. FIG. 4 is a plane view schematically showing a configuration for connecting the plurality of couplings 20 by the bus plate 33. FIG. 4 shows an example in which eight lanes are arranged in the analysis chip 10. That is, FIG. 4 shows a configuration in which the eight phoresis tanks 69 are aligned with one another with a predetermined pitch in the analysis chip 10.

The couplings 20 are attached to the respective phoresis tanks 69. The bus plate 33 including holes corresponding to the respective couplings 20 is prepared. That is, the bus plate 33 includes holes that are aligned at a predetermined pitch. The sleeves 22 of the couplings 20 are inserted into the holes of the bus plate 33, and are fixed by the nuts 30. According to this configuration, it is possible to supply the same voltage to the plurality of couplings 20 with a simple configuration. That is, since the electrodes 25 of the plurality of couplings 20 have the same potential, voltages for electrophoresis can be easily supplied even when electrophoresis is carried out in a plurality of lanes. It is therefore possible to easily carry out the size separation by electrophoresis.

The pipes 32 are connected to the respective couplings 20. Control valves 35 such as electromagnetic valves or the like are connected to the respective pipes 32. For example, the control valve 35 is supplied with compressed air supplied from a compressor or the like. By opening or closing the control valve 35, the supply of the gas from the pipe 32 is controlled. That is, to send the sample from the phoresis tank 69, the control valve 35 is opened. Accordingly, the gas from the coupling 20 is supplied to the phoresis tank 69 via the coupling 20. When the sample is not sent from the phoresis tank 69, the control valve 35 is closed. It is therefore possible to send the sample at appropriate timings. Further, it is possible to supply gas at the same time that the voltage is applied. Further, the discrete couplings 20 can be easily attached to the phoresis tank 69. Furthermore, since the pipe connection part 27 protrudes from the side part of the holder 21, the pipe 32 can be easily attached to the coupling 20 even when the plurality of phoresis tanks 69 are arranged.

While the coupling 20 connected to the phoresis tank 69 has been described above, the similar coupling 20 may be attached to the phoresis tank 71 as well. Further, the above described coupling 20 may be connected to any sample tank that stores the sample. According to this configuration, the gas and the voltage can be supplied from the through hole provided on the sample tank. It is therefore possible to easily supply the gas and the voltage at the same time. Further, by connecting the plurality of sleeves 22 by a bus electrode such as the bus plate 33, a voltage can be easily supplied to the plurality of sample tanks.

Modified Example

Figure 5:
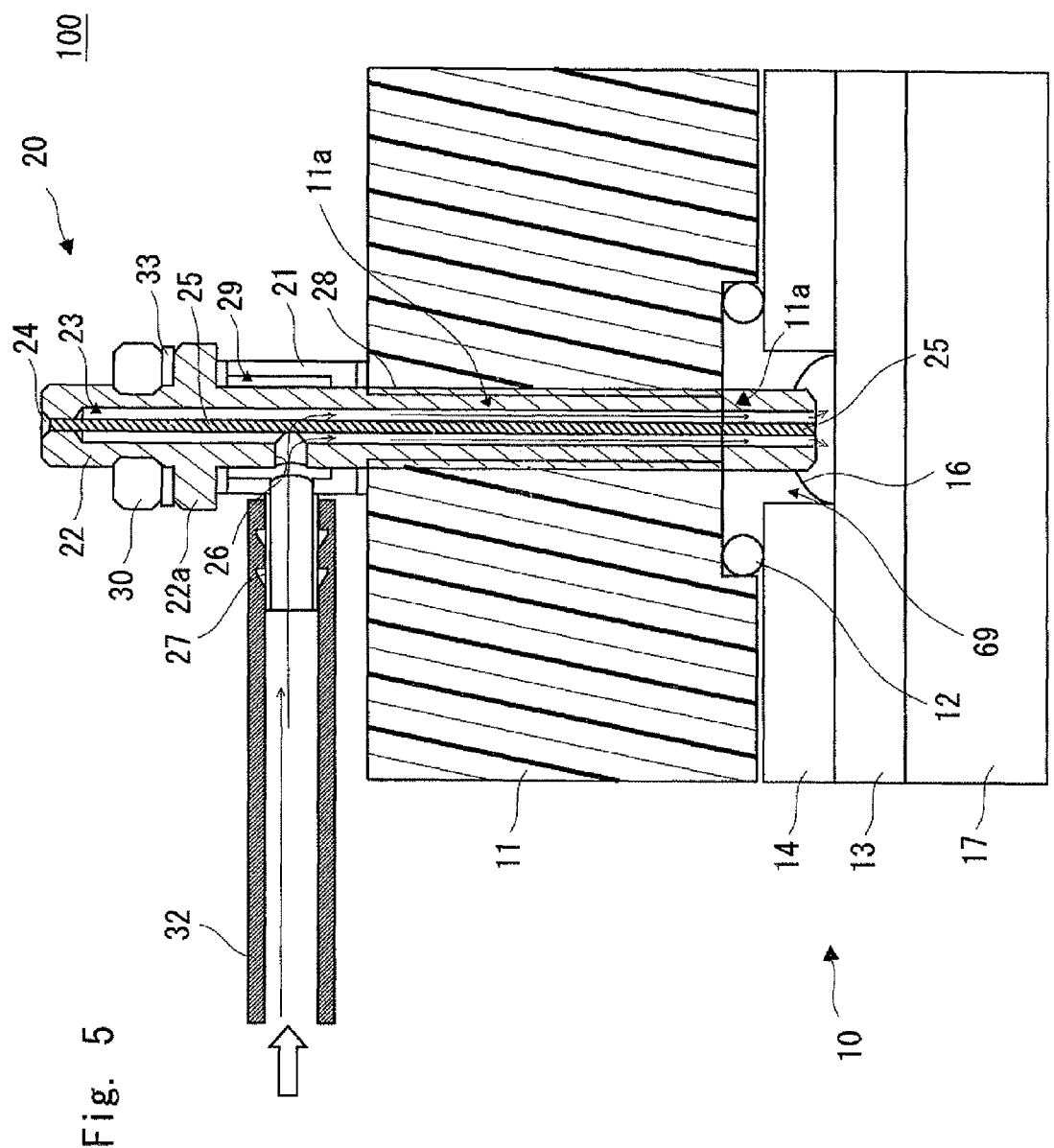
FIG. 5 is a side surface view showing an analysis device using a coupling according to a modified example.

FIG. 5 shows a modified example of the coupling 20. FIG. 5 is a side surface view showing an analysis device in a state in which the analysis chip 10 is placed on the placing board 17. In the modified example, the lengths of the electrode 25 and the sleeve 22 are substantially the same. Since the other configurations are similar to the above configurations, the descriptions thereof will be omitted as appropriate.

In FIG. 5, the height of the lower end of the sleeve 22 and that of the lower end of the electrode 25 are substantially the same. Besides the electrode 25, the sleeve 22 also penetrates through the sheet 16. In the configuration shown in FIG. 5, it is possible to directly spray the sample between the sheet 16 and the base plate 13 with gas. That is, gas to transfer the sample is supplied between the sheet 16 and the base plate 13. It is therefore possible to transfer the sample in the phoresis tank 69 to the channel.

While the present invention has been described above with reference to the exemplary embodiments, the present invention is not limited to the above exemplary embodiments. Various changes that can be understood by those skilled in the art may be made on the configurations or the details of the present invention within the scope of the present invention.

This application is based upon and claims the benefit of priority from Japanese Patent Application No. 2012-219262, filed on Oct. 1, 2012, the disclosure of which is incorporated herein in its entirety by reference.

REFERENCE SIGNS LIST

10 ANALYSIS CHIP
11 COVER
12 SEAL
13 BASE PLATE
14 MICROCHIP
16 SHEET
17 PLACING BOARD
20 COUPLING
21 HOLDER
22 SLEEVE
23 AIR CORE PART
24 FIXING PART
25 ELECTRODE
26 INLET PORT
27 PIPE CONNECTION PART
28 ATTACH PART
29 HOLLOW PART
30 NUT
32 PIPE
33 BUS PLATE
35 CONTROL VALVE
51 DNA EXTRACTION REGION
52 PCR AMPLIFICATION REGION
53 ELECTROPHORESIS REGION
60 SOLUTION
61 SAMPLE INJECTION TANK
62 WASH SOLUTION INJECTION TANK
63 PCR REAGENT INJECTION TANK
64 CHANNEL
65 MAGNETIC BEADS
66 OUTLET
67 EXTRACTION PART
68 PCR REACTION TANK
69 PHORESIS TANK
70 DETECTION POSITION
71 PHORESIS TANK

What is claimed is:

1. An analysis device comprising:
a placing board on which a chip is placed, the chip being supplied with a sample; and
a coupling that is attached to a cover, the cover covering the chip,
wherein the coupling comprises:
 a linear electrode;
 a sleeve comprising an attach part that is attached to the cover and an air core part in which the electrode is provided, the sleeve having a side surface in which a gas inlet port is provided, the gas inlet port communicating with the air core part; and
 a holder comprising a pipe connection part to which a pipe is connected, the pipe supplying gas to the gas inlet port, the holder holding the sleeve so as to surround the gas inlet port,
wherein the chip comprises a channel through which the sample flows and a plurality of sample tanks that communicates with the channel,
wherein the cover comprises a plurality of through holes correspondingly arranged above the plurality of the sample tanks,
wherein the plurality of the through holes corresponding to the plurality of sample tanks are provided in the cover,
wherein a screw hole is formed in a through hole of the plurality of through holes,
wherein a screw groove is provided in the attach part, the screw groove being screwed into the screw hole,
wherein the coupling is fixed to the through hole of the plurality of through holes by screwing the sleeve into the through hole, wherein the sample is one of liquid and gel, and
wherein the sample in a sample tank of the plurality of sample tanks is transferred to the channel by supplying gas to the sample tank through the air core part.

2. The analysis device according to claim 1, wherein the electrode projects to a bottom surface side of the chip further than the sleeve.

3. The analysis device according to claim 1, wherein electrodes of the plurality of couplings corresponding to the plurality of sample tanks are electrically connected by a bus electrode held in the sleeves of the plurality of couplings.

4. The analysis device according to claim 1, wherein the electrode and the sleeve are fixed to each other by welding or soldering.

5. The analysis device according to claim 1, comprising a control valve that is connected to the pipe and controls a supply of gas to the coupling.

* * * * *